(12) United States Patent
Freeman et al.

(10) Patent No.: US 10,617,347 B2
(45) Date of Patent: Apr. 14, 2020

(54) USING PH AND SMO$_2$ FROM A SPECTRAL SENSOR AS AN INDICATION OF SUBJECT DOWN TIME

(71) Applicant: ZOLL Medical Corporation, Chelmsford, MA (US)

(72) Inventors: Gary A. Freeman, Waltham, MA (US); Ulrich Herken, Medford, MA (US); Christopher L. Kaufman, Somerville, MA (US); Annemarie Elizabeth Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 150 days.

(21) Appl. No.: 15/076,192

(22) Filed: Mar. 21, 2016

(65) Prior Publication Data

US 2016/0278698 A1   Sep. 29, 2016

Related U.S. Application Data

(60) Provisional application No. 62/137,756, filed on Mar. 24, 2015.

(51) Int. Cl.
*A61B 5/00* (2006.01)
*A61B 5/1455* (2006.01)
(Continued)

(52) U.S. Cl.
CPC .......... *A61B 5/4836* (2013.01); *A61B 5/0075* (2013.01); *A61B 5/14551* (2013.01);
(Continued)

(58) Field of Classification Search
CPC .... A61B 5/021; A61B 5/14552; A61B 5/4836
See application file for complete search history.

(56) References Cited

U.S. PATENT DOCUMENTS 5,366,487 A * 11/1994 Adams ................. A61N 1/3621
600/518
7,096,064 B2   8/2006 Deno et al.
(Continued)

OTHER PUBLICATIONS

Bobrow, B. J., et al., "Minimally Interrupted Cardiac Resuscitation by Emergency Medical Services for Out-of-Hospital Cardiac Arrest," The Journal of the American Medical Association, vol. 299, No. 10, pp. 1158-1165, (Mar. 12, 2008).
(Continued)

*Primary Examiner* — Michael J D Abreu
(74) *Attorney, Agent, or Firm* — Fish & Richardson P.C.

(57) ABSTRACT

Embodiments of the present disclosure relate generally to the use of spectral sensors during a cardiac arrest event. More specifically, the present disclosure relates to the use of spectral sensors for measuring changes in pH and muscle oxygen saturation to estimate subject down time and evaluating the effectiveness of the clinical treatment administered during a cardiac arrest event. Given the narrow window of time in which emergency treatment must be administered, as well as the lack of information concerning the subject's condition, there is a need for a fast and accurate method of estimating the onset of the cardiac arrest emergency and evaluating the effectiveness of the emergency treatment being administered.

17 Claims, 9 Drawing Sheets

(51) Int. Cl.
*A61N 1/39* (2006.01)
*A61F 7/00* (2006.01)
*G01J 3/36* (2006.01)
*A61H 31/00* (2006.01)
*A61B 5/145* (2006.01)

(52) U.S. Cl.
CPC ............. *A61B 5/7282* (2013.01); *A61F 7/00* (2013.01); *A61N 1/3987* (2013.01); *G01J 3/36* (2013.01); *A61B 5/14535* (2013.01); *A61B 5/14539* (2013.01); *A61B 5/746* (2013.01); *A61F 2007/0093* (2013.01); *A61H 31/005* (2013.01); *A61H 31/006* (2013.01); *A61H 31/008* (2013.01); *A61H 2201/10* (2013.01); *A61H 2201/1207* (2013.01); *A61H 2201/5007* (2013.01); *A61H 2201/5025* (2013.01); *A61H 2201/5043* (2013.01); *A61H 2201/5058* (2013.01); *A61H 2201/5082* (2013.01); *A61H 2230/00* (2013.01); *A61H 2230/201* (2013.01); *A61H 2230/203* (2013.01); *A61H 2230/206* (2013.01)

(56) References Cited

U.S. PATENT DOCUMENTS

| | | | |
|---|---|---|---|
| 2009/0326356 A1* | 12/2009 | Kracker | A61B 5/0006 600/363 |
| 2011/0205535 A1 | 8/2011 | Soller et al. | |
| 2012/0232354 A1* | 9/2012 | Ecker | A61B 5/046 600/300 |

OTHER PUBLICATIONS

Weisfeldt, M. L. and Becker, L. B., "Resuscitation After Cardiac Arrest: A 3-Phase Time-Sensitive Model," The Journal of the American Medical Association, vol. 288, No. 23, pp. 3035-3038 (Dec. 18, 2002).

* cited by examiner

FIG. 1

Prior Art

FIG. 2

Prior Art

// USING PH AND SMO₂ FROM A SPECTRAL SENSOR AS AN INDICATION OF SUBJECT DOWN TIME

CROSS-REFERENCE TO RELATED APPLICATIONS

This application claims the benefit of U.S. Provisional Patent Application Ser. 62/137,756, filed on Mar. 24, 2015, entitled "Using Ph and SMO$_2$ From a Spectral Sensor as an Indication of Subject Down Time," which is incorporated herein by reference in its entirety for all purposes.

TECHNICAL FIELD

Embodiments of the present disclosure relate generally to the use of spectral sensors during a cardiac arrest event. More specifically, the present disclosure relates to the use of spectral sensors for measuring changes in pH and muscle oxygen saturation to estimate subject down time and evaluating the effectiveness of the clinical treatment administered during a cardiac arrest event.

BACKGROUND

Near-infrared radiation can generally pass through layers of skin and fat to illuminate blood vessels in muscle tissues. The radiation can be absorbed by hemoglobin in red blood cells, myoglobin in muscle fibers, water, and other proteins in blood plasma. Radiation is scattered by both muscle fibers and blood cells, and the scattered radiation can be detected and analyzed to determine the wavelength dependence of the scattered radiation. The absorbance spectrum of the various absorbing components in muscle tissues can be determined by comparing the spectra of incident radiation delivered to the tissues and the scattered radiation from the tissues. In some cases, particular spectral features in the absorbance spectrum can be assigned to particular components in the muscle tissues (e.g., certain spectral signatures can be assigned to absorption by hemoglobin and/or myoglobin).

During cardiac events such as ventricular fibrillation, pH and muscle oxygen saturation in tissues change, and these changes in pH and muscle oxygen saturation can reflect the physiological state of the subject, and may even have predictive value. In a typical cardiac arrest emergency situation, emergency medical assistance must be administered in a finite amount of time, and the decision as to what type of therapy to administer can be critical for the subject's survival. In many cases, there are no available witnesses to provide information about the cause of and circumstances surrounding the subject's condition. Given the narrow window of time in which emergency treatment must be administered, as well as the lack of information concerning the subject's condition, there is a need for a fast and accurate method of estimating the onset of the cardiac arrest emergency and evaluating the effectiveness of the emergency treatment being administered.

SUMMARY

A system for deriving an indication of subject down time according to embodiments of the present invention includes a spectral sensor, wherein the spectral sensor is configured for placement on skin of a subject above muscle tissue of the subject; a memory; a processor communicably coupled to the spectral sensor and the memory, the memory including instructions that, when executed by the processor, cause the processor to: determine muscle oxygen saturation of the muscle tissue with the spectral sensor; and estimate a length of the subject down time based on the muscle oxygen saturation.

A system for deriving an indication of subject down time according to embodiments of the present invention includes a spectral sensor, wherein the spectral sensor is configured for placement on skin of a subject above muscle tissue of the subject; a memory; a processor communicably coupled to the spectral sensor and the memory, the memory including instructions that, when executed by the processor, cause the processor to: determine pH of the muscle tissue with the spectral sensor; and estimate a length of the subject down time based on the pH of the muscle tissue.

A system for deriving an indication of subject down time according to embodiments of the present invention includes a spectral sensor, wherein the spectral sensor is configured for placement on skin of a subject above muscle tissue of the subject; a memory; a processor communicably coupled to the spectral sensor and the memory, the memory including instructions that, when executed by the processor, cause the processor to: determine muscle oxygen saturation and pH of the muscle tissue with the spectral sensor; estimate a first length of the subject down time based on the muscle oxygen saturation; estimate a second length of the subject down time based on the pH measurement; determine a composite length of the subject down time based on the first length and the second length.

A method for deriving an indication of subject down time according to embodiments of the present invention includes receiving spectral sensor data from a spectral sensor on skin of a subject above muscle tissue of the subject; determining muscle oxygen saturation of the muscle tissue with the spectral sensor data; and estimating a length of the subject down time based on the muscle oxygen saturation.

A method for deriving an indication of subject down time according to embodiments of the present invention includes receiving spectral sensor data from a spectral sensor on skin of a subject above muscle tissue of the subject; determining pH of the muscle tissue with the spectral sensor data; and estimating a length of the subject down time based on the pH of the muscle tissue.

A method for evaluating clinical treatment according to embodiments of the present invention includes receiving spectral sensor data from a spectral sensor on skin of a subject above muscle tissue of the subject; determining a muscle oxygen saturation measurement of the muscle tissue with the spectral sensor data at a first point in time; determining a muscle oxygen saturation measurement of the muscle tissue with the spectral sensor data at a second point in time; administering a clinical treatment to the subject between the first and second points in time; and based on a comparison of the muscle oxygen saturation measurements at the first and second points in time, visually indicating effectiveness of the clinical treatment.

A method for evaluating clinical treatment according to embodiments of the present invention includes receiving spectral sensor data from a spectral sensor on skin of a subject above muscle tissue of the subject; determining a pH measurement of the muscle tissue with the spectral sensor data at a first point in time; determining a pH measurement of the muscle tissue with the spectral sensor data at a second point in time; administering a clinical treatment to the subject between the first and second points in time; and based on a comparison of the pH measurements at the first and second points in time, visually indicating effectiveness of the clinical treatment.

A system for deriving an indication of subject down time according to embodiments of the present invention includes a spectral sensor, wherein the spectral sensor is configured for placement on skin of a subject above muscle tissue of the subject; a memory; a processor communicably coupled to the spectral sensor and the memory, the memory including instructions that, when executed by the processor, cause the processor to: determine muscle oxygen saturation of the muscle tissue with the spectral sensor; estimate a length of the subject down time based on the muscle oxygen saturation; and determine a phase of cardiac arrest based on the length of the subject down time.

A system for deriving an indication of subject down time according to embodiments of the present invention includes a spectral sensor, wherein the spectral sensor is configured for placement on skin of a subject above muscle tissue of the subject; a memory; a processor communicably coupled to the spectral sensor and the memory, the memory including instructions that, when executed by the processor, cause the processor to: determine pH of the muscle tissue with the spectral sensor; estimate a length of the subject down time based on the pH of the muscle tissue; and determine a phase of cardiac arrest based on the length of the subject down time.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

There are several different implementations of the invention possible. Some possible implementations are described herein; however, as one of ordinary skill in the art would appreciate, these are exemplary implementations of the invention, which is not limited to the detailed examples provided.

An embodiment of the invention includes a patient monitoring and control system including one or more spectral sensors. The spectral sensors may include a muscle oxygen saturation (SmO2) sensor, a pH sensor, a blood hematocrit sensor, a carbon dioxide sensor, and/or other sensors capable of obtaining clinical characteristics of a patient. Such clinical characteristics may include muscle tissue oxygen saturation (SmO2), pH, hematocrit level, carbon dioxide levels, and the like. The one or more spectral sensors may comprise both long-distance and short-distance radiation sources to allow for differing depth of penetration into the skin and/or tissue of the subject. The clinical characteristics may be used to estimate the onset of the subject's cardiac event, also known as the subject's down time (e.g., the elapsed time since the onset of ventricular fibrillation). Determining one or more of a subject's clinical characteristics after experiencing a cardiac event can aid medical personnel in the determination of the best treatment options to pursue subsequent to that cardiac event. For example, determining a subject's down time can be useful for determining whether or not to administer defibrillation therapy, CPR, and/or the like. The one or more spectral sensors may be communicably coupled with a patient monitor, which may include a defibrillator or an automatic external defibrillator, a stand-alone monitor, a hand held monitor, a remote monitor, and/or the like. A patient monitor may include or otherwise be in communication with a processor, which is configured to or otherwise capable of executing all or parts of the methods described herein and/or described in U.S. Publication No. 2011/0205535 ("the '535 Publication"), "SPECTROSCOPIC SENSORS," filed on May 3, 2011, and assigned to University of Massachusetts, the entirety of which is hereby incorporated herein for all purposes.

Figure 1:
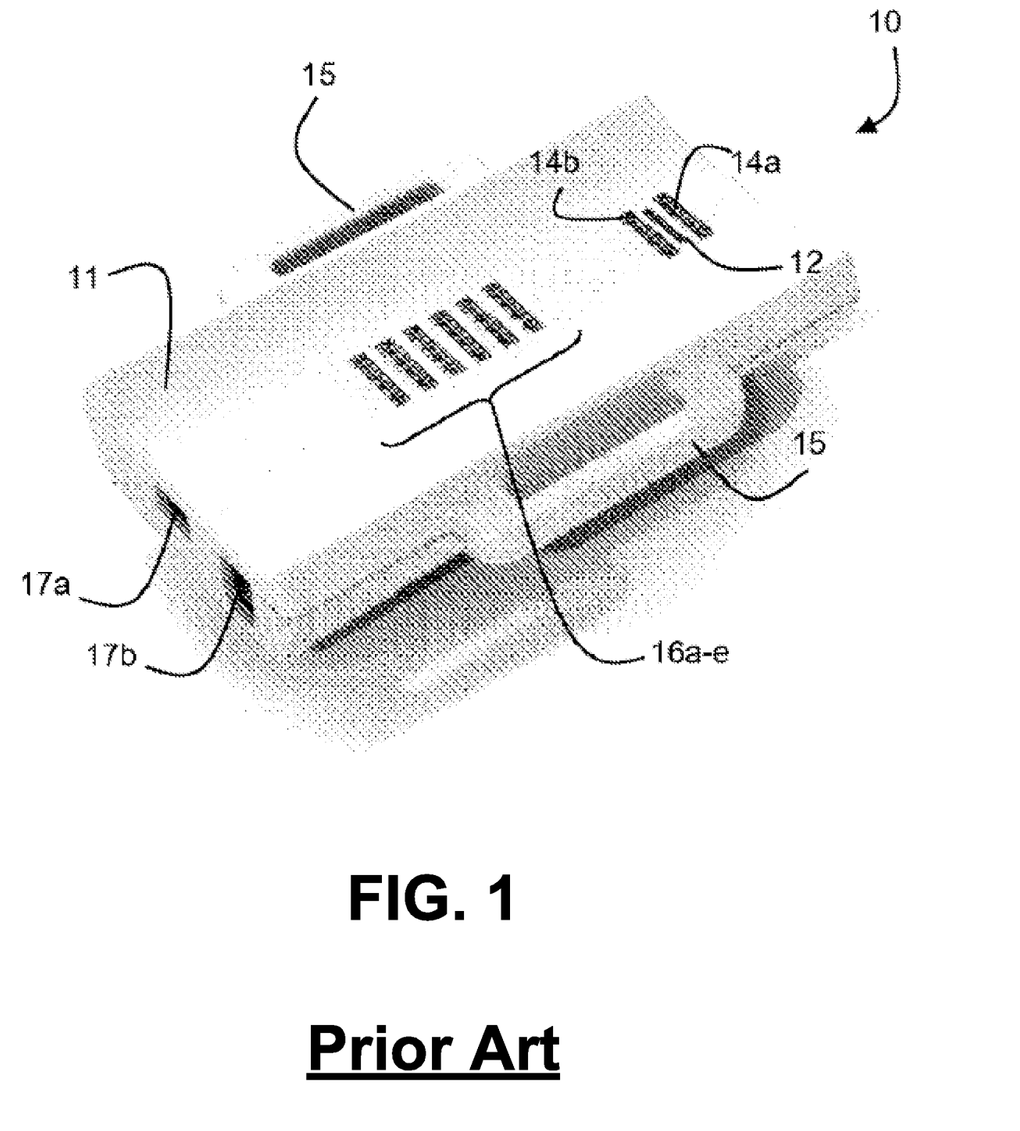
FIG. 1 illustrates a prior art spectral sensor.
Figure 2:
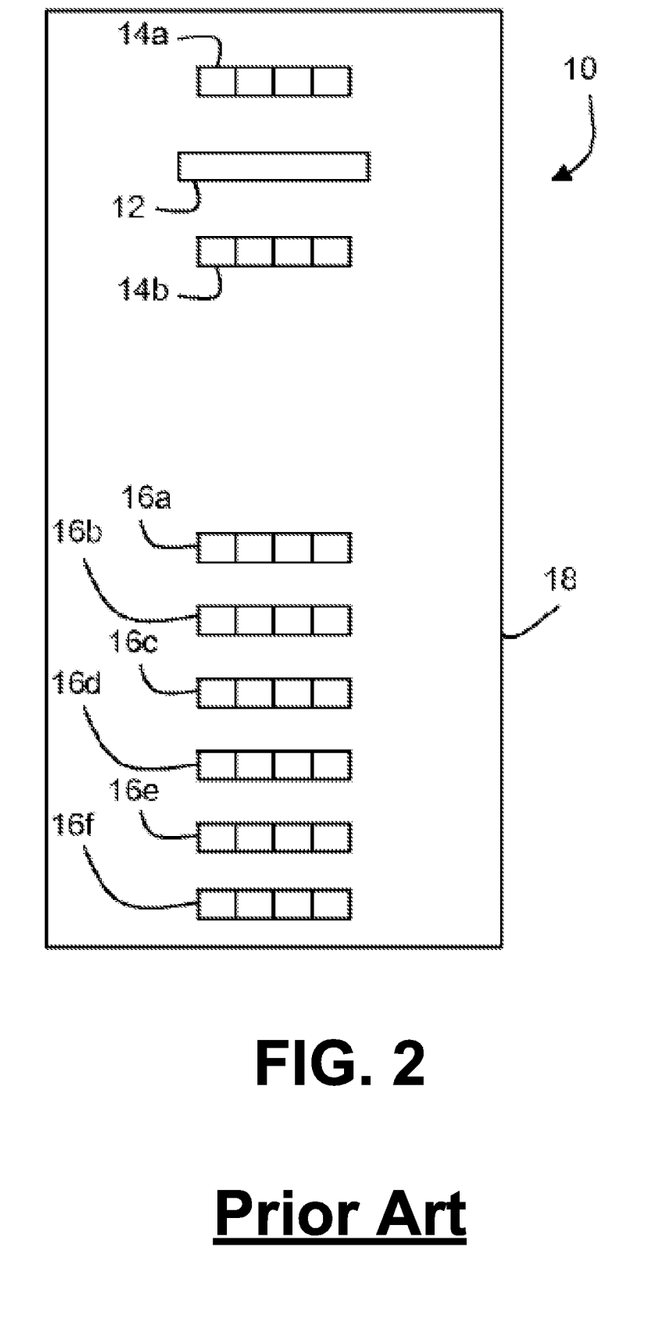
FIG. 2 illustrates a bottom schematic view of placement of radiation sources and a detector of the prior art spectral sensor of FIG. 1.
Figure 3:
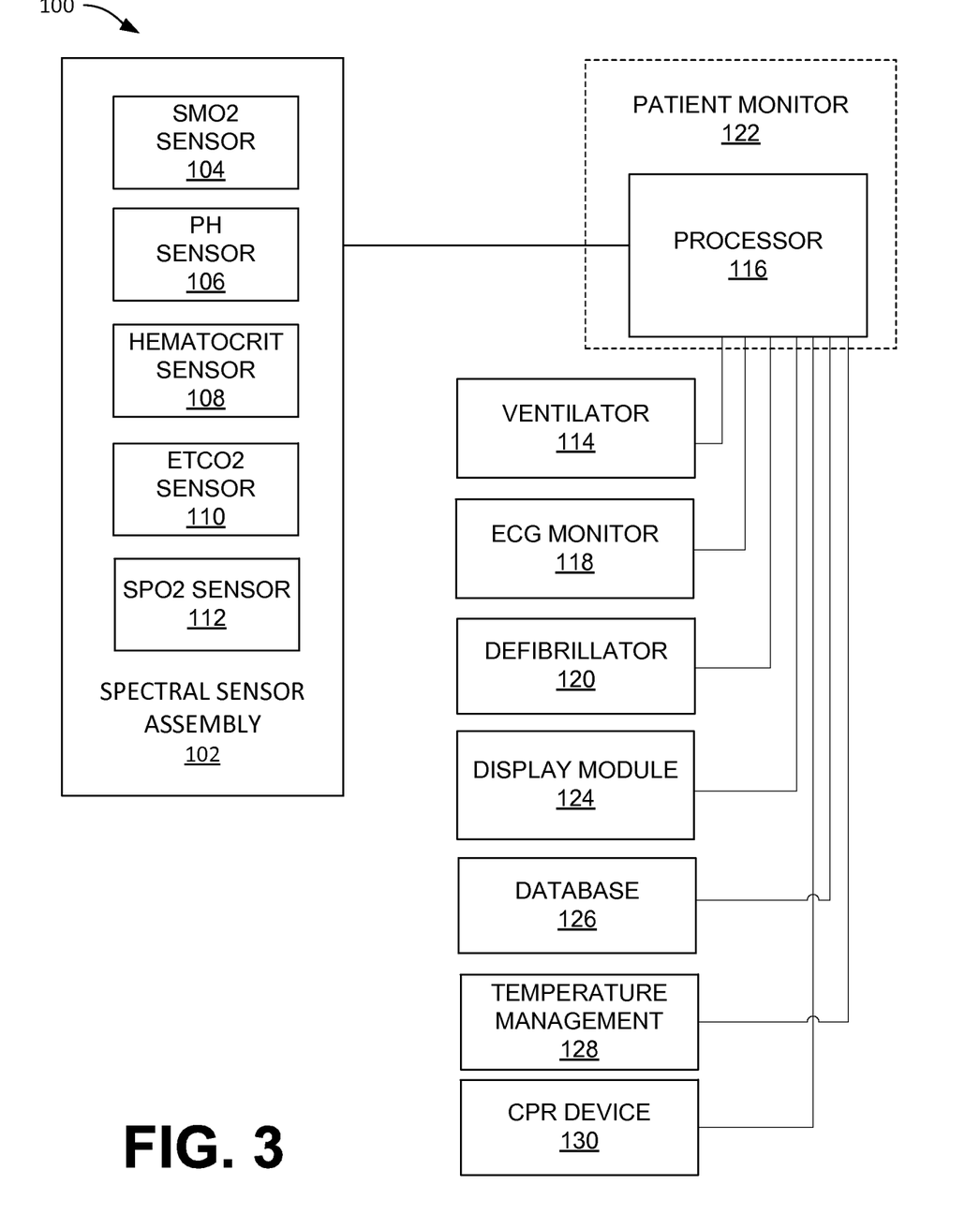
FIG. 3 illustrates a patient monitoring and spectral sensing system, according to an embodiment of the present disclosure.

FIG. 3 illustrates a patient monitoring and control system 100 including a spectral sensor assembly 102, according to embodiments of the present invention. The spectral sensor assembly 102 may include a muscle oxygen saturation ($SmO_2$) sensor 104, a pH sensor 106, a blood hematocrit sensor 108, a carbon dioxide ($CO_2$) sensor 110, and/or a pulse oximetry ($SpO_2$) sensor 112 (referred to interchangeably herein as a "pulse oximeter"), according to embodiments of the present invention. In embodiments, the spectral sensors 104, 106, 108, 110, 112 may each be part of the common spectral sensor assembly 102 that observes infrared spectroscopy characteristics of a subject's blood, to which the processor 116 may apply various algorithms to calculate and output $SmO_2$, pH, hematocrit values, $ETCO_2$, and/or $SpO_2$. In embodiments, any one or more of the sensors 104, 106, 108, 110, and 112 may be independent sensor devices. According to embodiments, any of the sensors 10, 102, or others described herein may include any or a subset of the hardware, software, characteristics, and/or performance of any of the spectral sensors and related functionality described in the '535 Publication.

For example, a spectral sensor assembly 102 may include an optical bench that houses spectral sensors capable of obtaining various types of measurements such as $SmO_2$ and/or pH, and the system 100 may include, for example, a separate pulse oximeter 112, and the $ETCO_2$ sensor 108 may be integrated with a ventilator 114. In embodiments, the optical bench may include one or more long-distance radiation sources, one or more short-distance radiation sources, and one or more spectral detectors. That is, radiation sources may be located on the spectral sensor assembly at different distances from the spectral detector to facilitate obtaining measurements at various tissue depths. Radiation sources located closer to the spectral detector than other radiation sources may be referred to as "short-distance" radiation sources, and radiation sources that are located farther away from the spectral detector may be referred to as "long-distance" radiation sources. For example, scattered radiation spectra derived from long-distance radiation sources typically include spectral contributions from both muscle tissues within the sample, and from layers of skin and/or fat positioned between the sensor and the muscle tissues. Typically, scattered radiation spectra derived from short-distance radiation sources include spectral contributions substantially only from the layers of skin and/or fat positioned between the sensor and the muscle tissues. Various embodiments of long-distance and short-distance sensors are described, for example, in the '535 Publication.

The one or more long-distance radiation sources, the one or more short-distance radiation sources, and the spectral detector are coupled to an optical bench disposed on a tissue-facing side of a sensor module (e.g., the spectral sensor assembly 102, or a housing thereof). In embodiments, the spectral sensor assembly 102 may be adapted to be applied to an extremity of a child. That is, for example, a sensor module may be about one inch wide, about three inches long, and about ¼ inch thick, or roughly about the same size and shape as a BandAid.

In embodiments, the spectral sensors 104, 106, 108, 110, 112, and the ventilator 114 may communicate with a processor 116. The processor 116 may represent one or more processors 116 that may be disposed in one or more devices. The processor 116 may be one or more hardware processors, one or more software processors, and/or one or more combinations thereof. For example, the processor 116, an ECG monitor 118, and a defibrillator 120 may all be integrated into a patient monitor 122 such as, for example, an X-Series Patient Monitor/Defibrillator, available from ZOLL® Medical. For example, the processor 116 may be communicably coupled to the one or more long-distance radiation sources and the one or more short-distance radiation sources and may be configured to determine a first pH measurement of underlying muscle tissue at a first depth; determine a second pH measurement of the underlying muscle tissue at a second depth; and identify, based on the first and second pH measurements, a level of degeneration in the muscle tissue. In embodiments, the level of degeneration may facilitate determining whether the subject is undergoing arrhythmia arrest or asphyxia arrest. In embodiments, other acute conditions may be detectable as well. For example, if a subject is experiencing asystole and has a very low pH, a clinician may be encouraged to determine whether that subject has a pulmonary embolism.

As indicated above, the patient monitor 122 may be, for example, a defibrillator or an automatic external defibrillator, according to embodiments of the present invention. The patient monitor 122 may include, or otherwise be in communication with, a processor 116, which is configured to execute, or is otherwise capable of executing, all or parts of embodiments of methods described herein and/or described in the '535 Publication. The patient monitor 122 may have its own display module 124 in communication therewith, and/or the system 100 may include a separate display module 124, according to embodiments of the present invention.

Information about the physiological parameters as measured, or measured over time, by one or more spectral sensors, such as those included in the spectral sensor assembly 102 may be displayed on the display module 124 of the patient monitor 122 and/or the other display module 124, for example along with other data about a subject to which the spectral sensor assembly 102 is applied, according to embodiments of the present invention. Such data or information may also be stored in a database 126, for example, independently or with other information about the subject or the medical encounter for which the spectral sensor assembly 102 is being utilized. Processor 116 may be communicably coupled to a temperature management system 128, for example the Thermogard XP® Temperature Management System available from ZOLL Medical Corporation. Processor 116 may further be communicably coupled to a cardiopulmonary resuscitation device 130, for example an AutoPulse® Non-Invasive Cardiac Support Pump available from ZOLL Medical Corporation. The hardware, software, and/or firmware elements and/or modules shown in FIG. 3 may be included on the same device and/or distributed across multiple devices, and each such element or module shown in FIG. 3 may have its elements or functionality spread across multiple devices.

The illustrative system 100 shown in FIG. 3 is not intended to suggest any limitation as to the scope of use or functionality of embodiments of the present invention. Neither should it be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present invention.

Figure 4:
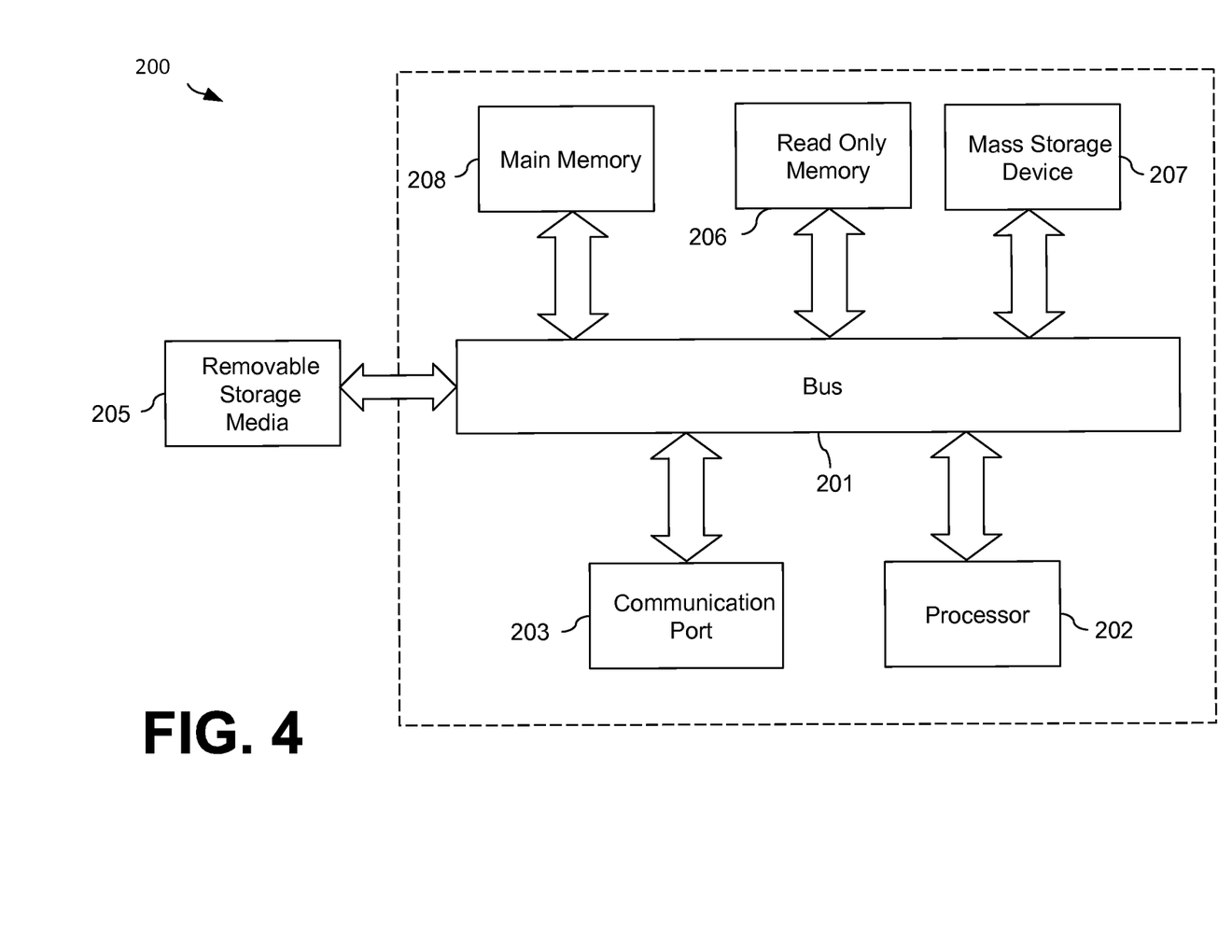
FIG. 4 illustrates a computer system.

FIG. 4 is an example of a computer system 200 with which embodiments of the present invention may be utilized. The computer system 200 may represent, for example, one or more computing devices, one or more components of computing devices, and/or the like. For example, any one or more of the components illustrated in FIG. 3 may be, incorporate, or be incorporated within, a computer system 200, according to embodiments of the present invention. According to the present example, the computer system 200 includes a bus 201, at least one processor 202, at least one communication port 203, a main memory 208, a removable storage media 205, a read only memory 206, and a mass storage 207.

Processor(s) 202 can be any known processor, or any known microprocessor or processor. Communication port(s) 203 can be, or include, any number of different types of communication ports such as, for example, an RS-232 port for use with a modem based dialup connection, a copper or fiber 10/100/1000 Ethernet port, a Bluetooth® or WiFi interface, and/or the like. Communication port(s) 203 may be chosen depending on a network such a Local Area Network (LAN), Wide Area Network (WAN), or any network to which the computer system 200 connects. Main memory 208 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as SCSI drives, an optical disc, an array of disks such as RAID, or any other mass storage devices may be used. Bus 201 communicably couples processor(s) 202 with the other memory, storage and communication blocks, and may, in embodiments, include one or more busses. Bus 201 can be, or include, a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 200 and related components.

Figure 5:
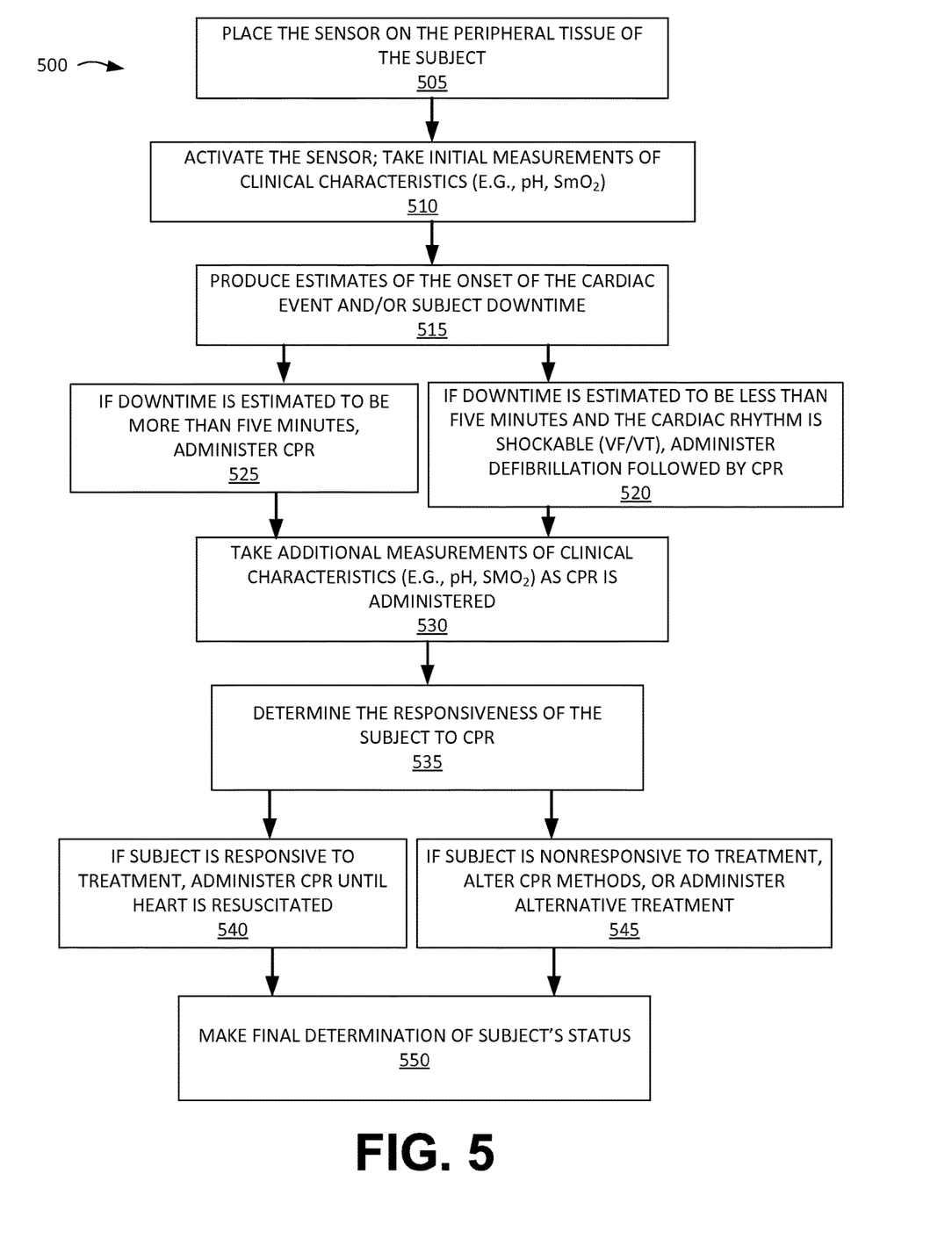
FIG. 5 is a flow chart representing a method of administering emergency treatment to a subject experiencing a cardiac event, according to one embodiment of the present disclosure.

Referring to FIG. 5, an embodiment of a method 500 of administering treatment to a subject following a cardiac event is shown. Generally, the method 500 uses one or more spectral sensors described above to measure one or more clinically useful characteristics of a subject experiencing a cardiac event, including, for example, muscle oxygen saturation ($SmO_2$) and pH. Tissue oxygen saturation can be indicative of how much oxygen a subject's body is consuming, with levels below 60% generally indicating that the subject is at risk of ischemic diseases. During cardiac events, such as ventricular fibrillation, peripheral $SmO_2$ levels have been shown to decrease after the onset of the cardiac event, as the subject's fibrillating heart struggles to supply oxygenated blood to surrounding tissues. If a reduction in oxygenation in a tissue is not rapidly reversed, the pH of the subject's tissues will decrease (e.g., as lactate builds). Additionally, resuscitation to restore normal oxygen levels in the tissue without also restoring normal pH levels can be detrimental to the subject's recovery. As mentioned above, spectral sensors can be used to measure $SmO_2$ and pH levels in a subject experiencing a cardiac event.

As used herein, the term "subject" is used in its broadest sense and generally includes, but is not limited to, mammals, including a human, a non-human primate, a mouse, a pig, a cow, a goat, a cat, a rabbit, a rat, a guinea pig, a hamster, a degu, a horse, a monkey, a sheep, and/or other non-human mammal. The term "subject" also refers to, without limitation, any of the aforementioned examples that may be in need of treatment for a cardiac event, or is being evaluated as part of experiments relating to treatments for a cardiac event.

As shown in FIG. 5, the method 500 of administering treatment to a subject following a cardiac event according to embodiments of the present disclosure comprises placing a spectral sensor assembly 102, or one or more spectral sensors, on the peripheral tissue of the subject in need of medical attention, as shown at 505. Peripheral tissue may include any tissue that is peripheral to the area of the subject's body surrounding the subject's heart, including for example, the subject's arm, leg, hip, chest, or back. The spectral sensors may be part of a spectral assembly, and are typically placed on a subject's skin above the muscle tissue of the subject. The one or more spectral sensors may comprise both long-distance and short-distance radiation sources to allow for differing depth of penetration into the skin and/or tissue of the subject. For example, the spectral sensor assembly 102 may include one or more, preferably two or more, long-distance radiation sources and one or more short-distance radiation sources. Before activating the spectral sensor and measuring one or more characteristics of the subject, the spectral sensor may require calibration or repositioning.

At 510, the one or more spectral sensors are activated and initial measurements of the relevant clinical characteristics of the subject are taken. The spectral sensor can be used to measure $SmO_2$ and pH levels in peripheral tissue, such as muscle tissue, at a first point in time. This initial measurement can be done once the sensor is activated and prior to administering any emergency treatment.

Next, at 515, this initial measurement can be used to estimate the onset of the subject's cardiac event, also known as the subject's down time (e.g., the elapsed time since the onset of ventricular fibrillation). This estimate can be obtained, for example, by comparing the value of the particular subject's clinical characteristic to a predetermined model. For example, the initial $SmO_2$ measurement of a particular subject can be compared to a model (e.g., a mathematical model) correlating $SmO_2$ over time. Using the model, the subject's initial $SmO_2$ measurement can be put into a clinically relevant context and used to determine, for example, the subject's down time. The model may be based on a plurality of measurements taken for a particular subject; the model may be based on a plurality of measurements taken on one or more subjects in a similar demographic (e.g., pediatric subjects); and/or the model may be based on a plurality of measurements taken on one or more subjects possessing a common suite of physiological characteristics (e.g., predisposition to atherosclerosis, high blood pressure, and the like). Other relevant models can readily be determined by one of ordinary skill in the art cardiovascular medicine, including, but not limited to, models correlating pH levels over time, lactate levels over time, and phosphate levels over time.

Determining one or more of a subject's clinical characteristics after experiencing a cardiac event can aide medical personnel in the determination of the best treatment options to pursue subsequent to that cardiac event. For example, determining a subject's down time can be useful for determining whether or not to administer defibrillation therapy. As shown at 515, the sensor can produce an estimate of a subject's down time. In some cases, the sensor can produce a specific estimate of a subject's down time in minutes or seconds. In other cases, the sensor can produce a binary indication of a subject's need for certain therapy, such as defibrillation therapy. For example, clinical observations suggest that subjects are likely to respond well to transthoracic defibrillation if less than four minutes have elapsed since the onset of ventricular fibrillation and to respond poorly if more than seven minutes have elapsed. Other observations suggest that five minutes is the approximate boundary between a probable successful defibrillation and a probable lack of success in the absence of therapeutic intervention. Therefore, depending on the subject and the model used, the sensor can indicate a need for defibrillation therapy to be administered if, for example, the down time is estimated to be less than five minutes and the cardiac rhythm is shockable (e.g., if the cardiac rhythm is characterized by ventricular fibrillation (VF) or ventricular tachycardia (VT)) (520). If down time is estimated to be more than five minutes, the sensor can indicate a need to bypass defibrillation therapy and instead proceed directly to the administration of CPR (525).

The continual measurement or monitoring of relevant clinical characteristics of a subject experiencing a cardiac event can be used to evaluate the effectiveness of the therapy being administered. For example, at 530, the method 500 of FIG. 5 includes measuring pH or $SmO_2$ levels at a second point in time, after CPR therapy has begun being administered to the subject. The sensor can indicate if the subject is responding to CPR treatment by visually tracking increases in pH or $SmO_2$ levels in the subject over time, as shown at 535. If the subject is responsive to the treatment, the sensor can indicate that CPR treatment should continue until the subject's heart is resuscitated (540). As shown at 545, if the subject is nonresponsive to CPR treatment, the sensor can indicate that CPR treatment should cease and that an alternative treatment may be administered (e.g., pharmacological intervention).

Finally, at 550, the sensor can be equipped to indicate whether the clinical characteristics being monitored or measured have reached a certain threshold indicating the subject's heart has been resuscitated or that the subject's heart is nonresponsive.

Generally, embodiments of this method may be performed trained medical personnel, such as a first responder or an emergency room physician. However, in the absence of such a person, embodiments of the method can be performed by a medical lay person that has access to the spectral sensor described herein and who can perform CPR.

Additionally, as can be appreciated by one of ordinary skill in the art of cardiovascular medicine, the method described herein can include a separate spectral sensor designed to measure or monitor specific clinical characteristics of a subject's heart who is experiencing a cardiac event. In some cases, the spectral sensor described above for peripheral tissue monitoring can be used in conjunction with a spectral sensor for monitoring a subject's heart. In some embodiments, data is obtained using such sensors and combined and/or correlated to increase the accuracy or efficiency of the methods described above.

EXAMPLES

The present disclosure is more particularly described in the following examples that are intended as illustrations only, since numerous modifications and variations within the scope of the present disclosure will be apparent to those of skill in the art.

Figure 6:
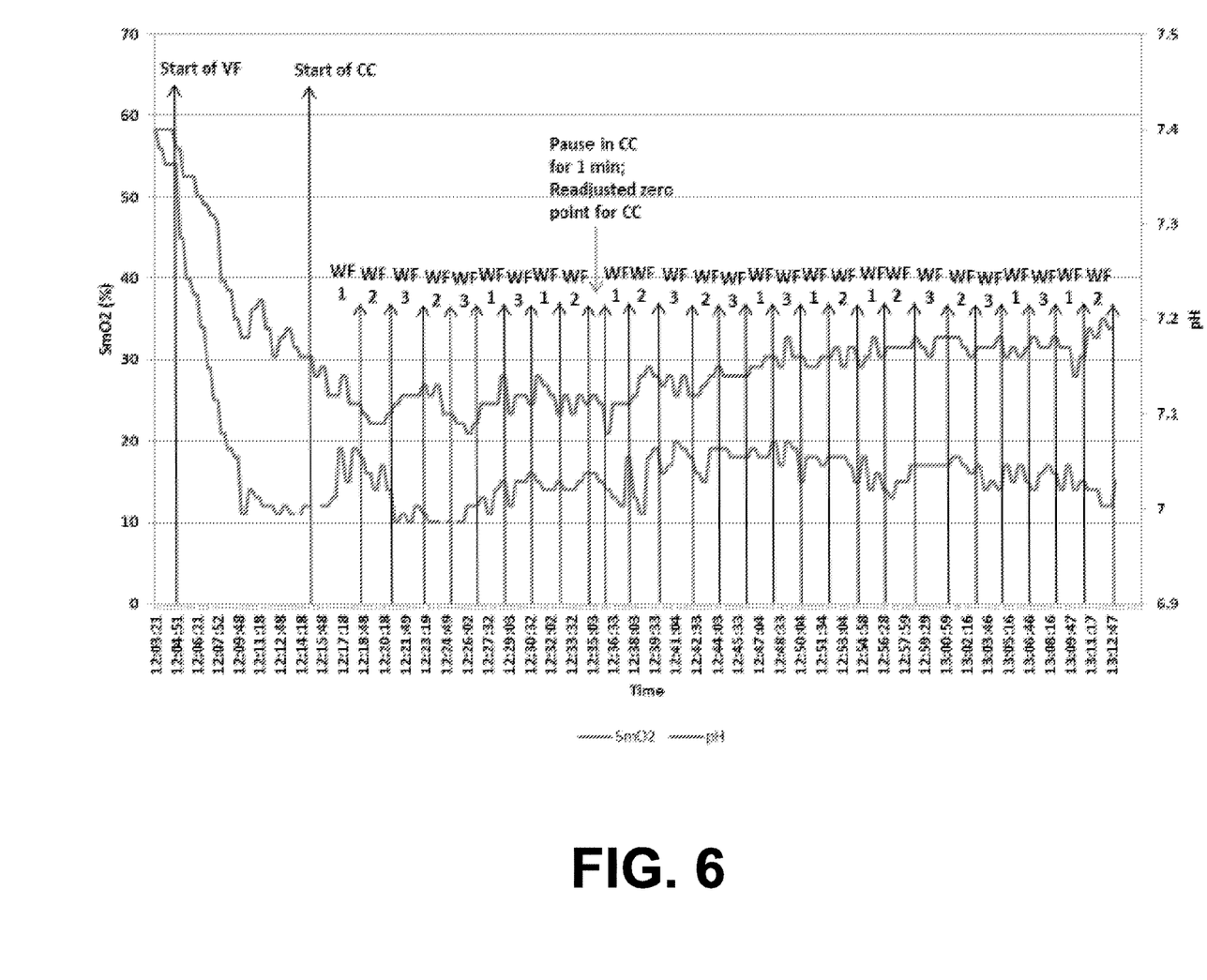
FIG. 6 is a graphical representation of a first test subject receiving treatment after experiencing a cardiac event, according to one embodiment of the present disclosure.

Example 1: Change in $SmO_2$ and pH During 10 Minutes of Untreated VF Followed by 54 Minutes of CPR in a First Swine Test Subject FIG. 6 is a graphical representation of a first test subject receiving treatment after experiencing a cardiac event, according to one embodiment of the present disclosure. The data represented was taken from a swine model after electrically inducing ventricular fibrillation (VF) at about time point 12:04:51. A spectral sensor was placed on the biceps femoris of the right rear leg of the swine. VF was left untreated (i.e., no CPR) for ten minutes, after which chest compressions (CC) were started. The depth of the chest compressions were at 1 inch for the first minute, 1.5 inches for the second minute, and 1.9 inches for rest of the experiment. Release time for the chest compressions was changed every two minutes. Release times were 100 msecs, 200 msecs, or 300 msecs (WF1, WF2, and WF3, respectively). Additionally, a one minute pause in chest compressions was used to readjust the zero point for subsequent chest compressions, as the chest had undergone remodeling as a result of the continuous chest compressions. Percentage of $SmO_2$ is represented on the left y-axis; pH is represented on the right y-axis; and time is represented on the x-axis. The red line corresponds to the continuous pH measurements, and the blue line corresponds to the continuous $SmO_2$ measurements.

As shown in FIG. 6, $SmO_2$ progressively decreased after the induction of VF (i.e., due to the creation of a low-flow hemodynamic state). $SmO_2$ reached a minimal value after approximately five minutes of untreated VF, and this level was generally maintained until the start of chest compressions. pH decreased progressively as well, though the slope was not as steep. However, $SmO_2$ and pH increased progressively after the start of chest compressions, indicating that the test subject was responsive to CPR treatment.

Figure 7:
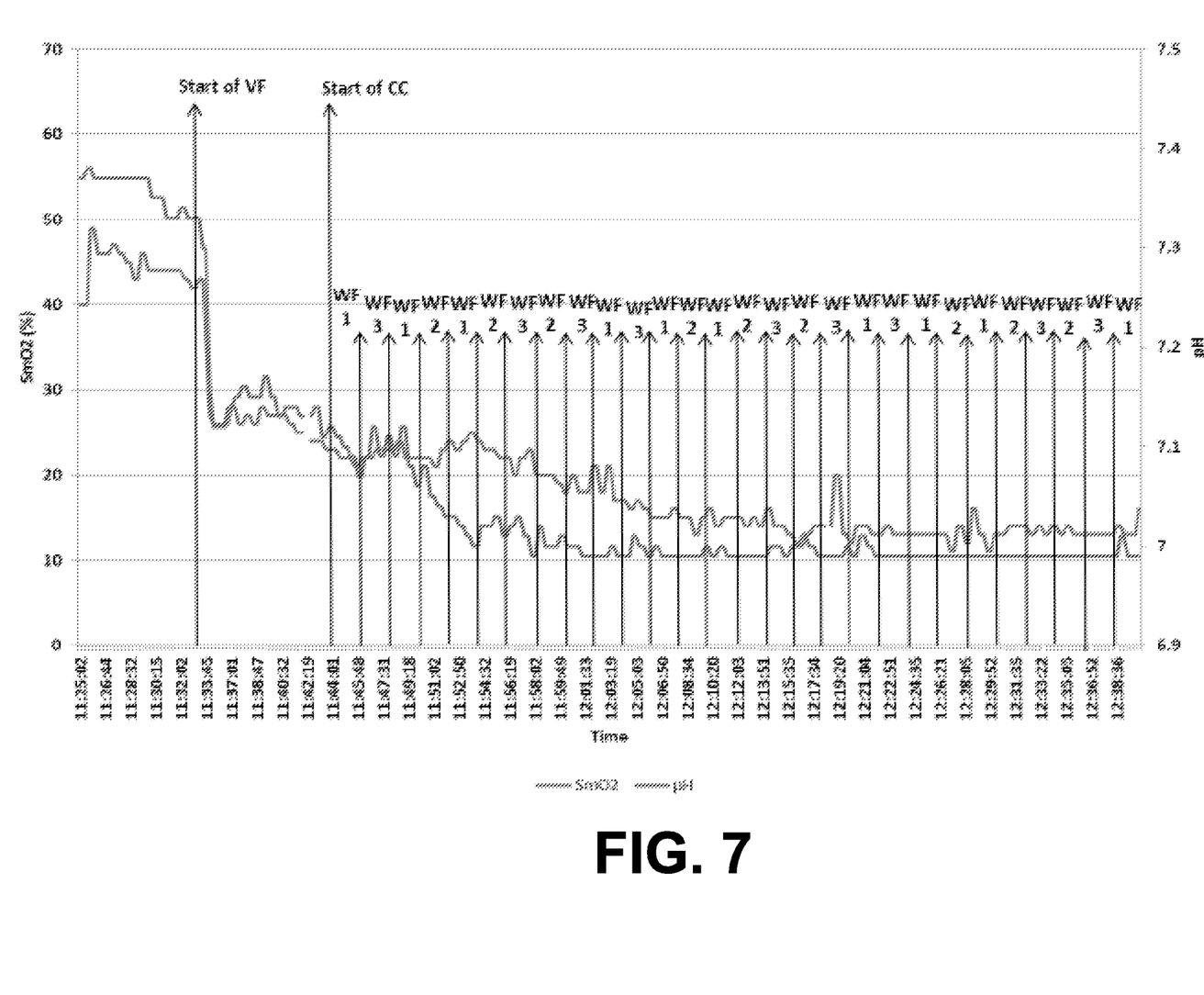
FIG. 7 is a graphical representation of a second test subject receiving treatment after experiencing a cardiac event, according to one embodiment of the present disclosure.

Example 2: Change in $SmO_2$ and pH During 10 Minutes of Untreated VF Followed by 54 Minutes of CPR in a Second Swine Test Subject FIG. 7 is a graphical representation of a second test subject receiving treatment after experiencing a cardiac event, according to one embodiment of the present disclosure. The data represented was taken from a swine model after electrically inducing ventricular fibrillation (VF) at about time point 11:33:00. A spectral sensor was placed on the bicep femoris of the right rear leg of the swine. VF was left untreated (i.e., no CPR) for ten minutes, after which chest compressions (CC) were started. The depth of the chest compressions were at 1 inch for the first minute, 1.5 inches for the second minute, and 1.9 inches for rest of the experiment. Release time for the chest compressions was changed every two minutes. Release times were 100 msecs, 200 msecs, or 300 msecs (WF1, WF2, and WF3, respectively). Percentage of $SmO_2$ is represented on the left y-axis; pH is represented on the right y-axis; and time is represented on the x-axis. The red line corresponds to the continuous pH measurements, and the blue corresponds to the continuous $SmO_2$ measurements.

As shown in FIG. 7, both pH and $SmO_2$ progressively declined after the induction of VF (i.e., due to the creation of a low-flow hemodynamic state), though not as dramatically as the first test subject. However, unlike the first test subject, pH and $SmO_2$ did not progressively increase after the start of chest compressions, but continued a downward trend, leveling off at about a pH of 7.0 and an $SmO_2$ between about 12-13%. These data indicate that the test subject was nonresponsive to CPR treatment, and suggest the need for alternative cardiac intervention (e.g., pharmacological intervention or a different chest compression waveform/depth).

Figure 8:
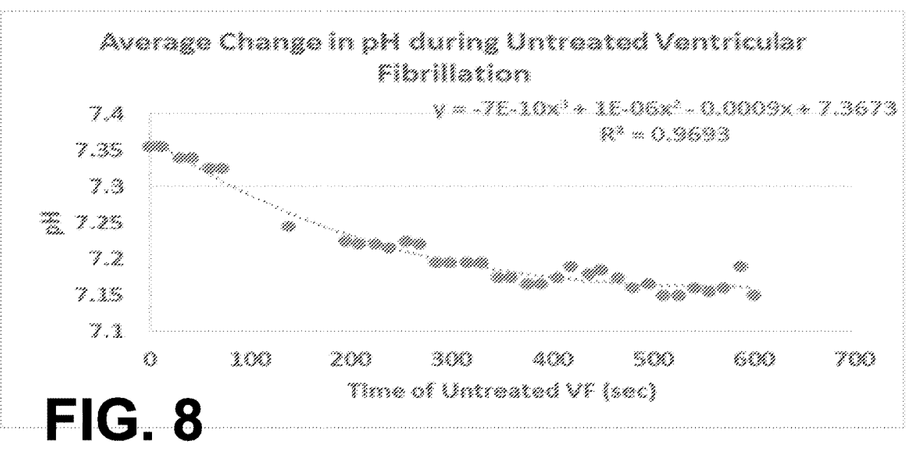
FIG. 8 is a graphical representation of an average pH of the first and second tests of FIGS. 6 and 7 with a curve fit over time.

As illustrated in the above examples, both pH and $SmO_2$ correlate with subject down time in untreated ventricular fibrillation. FIG. 8 illustrates a graphical representation of an average pH of the first and second examples (described above with respect to FIGS. 6 and 7) over time. Applying a curve fit to the data of FIG. 8 in order to derive an equation or correlation may be achieved with various statistical analysis methods known in the art. Applying one such curve fit leads to one possible equation for estimating or determining the time, in seconds, since onset of untreated ventricular fibrillation based on the subject's tissue pH measurement (taken, for example, using a spectral sensor or optical spectroscope as described herein), as follows in Equation 1:

$$y = -7E-10x^3 + 1E-06x^2 - 0.0009x + 7.3673 \quad \text{(Eq. 1)}$$

in which y is the down time in seconds, and x is the pH, with an $R^2$ value of 0.9693.

Figure 9:
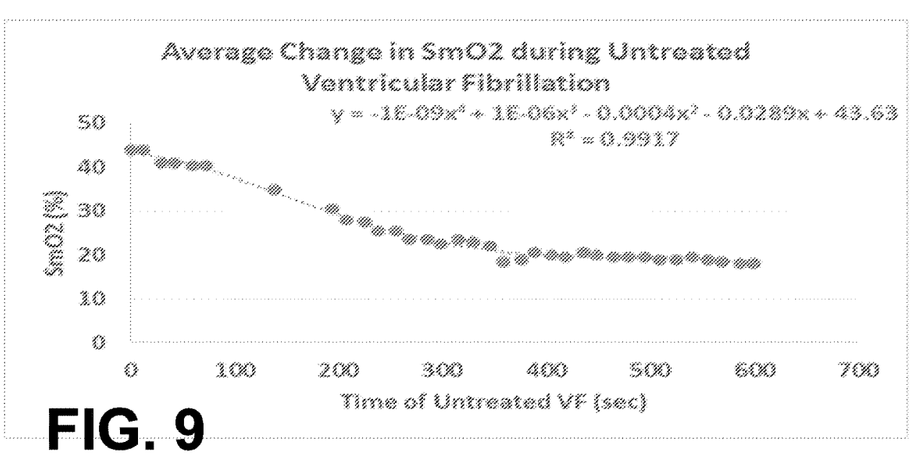
FIG. 9 is a graphical representation of an average muscle oxygen saturation of the first and second tests of FIGS. 6 and 7 with a curve fit over time.

FIG. 9 is a graphical representation of an average muscle oxygen saturation of the first and second examples (described above with respect to FIGS. 6 and 7) over time. Applying a curve fit to the data of FIG. 9 in order to derive an equation or correlation may be achieved with various statistical analysis methods known in the art. Applying one such curve fit leads to one possible equation for estimating or determining the time, in seconds, since onset of untreated ventricular fibrillation based on the subject's tissue muscle oxygen saturation measurement (taken, for example, using a spectral sensor or optical spectroscope as described herein), as follows in Equation 2:

$$y = -1E-09x^4 + 1E-06x^3 - 0.0004x^2 - 0.0289x + 43.63 \quad \text{(Eq. 2)}$$

in which y is the down time in seconds, and x is the $SMO_2$ as a percentage, with an $R^2$ value of 0.9917.

Various authors and researchers have demonstrated that particularizing the treatment protocol to the down time or cardiac arrest phase of the subject can improve outcomes. See, for example, "Minimally Interrupted Cardiac Resuscitation by Emergency Medical Services for Out-of-Hospital Cardiac Arrest," Bobrow, Bentley J., M.D., et al., Journal of the American Medical Association, vol. 299, no. 10, Mar. 12, 2008, pp. 1158-1165, which is incorporated by reference herein. Another article, "Resuscitation After Cardiac Arrest," Weisfeldt, Myron L., M.D., et al., Journal of the American Medical Association, vol. 288, no. 23, Dec. 18, 2002, pp. 3035-3038, which is also incorporated by reference herein, describes a three-phase time-sensitive model for resuscitation after cardiac arrest. For example, those authors describe an "electrical phase" occurring approximately within four minutes of the onset of ventricular fibrillation or cardiac arrest, a "circulatory phase" occurring approximately four to ten minutes after onset of cardiac arrest, and a "metabolic phase" occurring after approximately ten minutes after onset of cardiac arrest. Those authors suggest that, during the electrical phase, rapid defibrillation leads to better patient outcomes; they also suggest that, during the circulatory phase, applying chest compression (or chest compression and epinephrine) prior to defibrillation leads to better patient outcomes; finally, they also suggest that, during the metabolic phase, cooling the subject or providing hypothermia-based treatment to the subject prior to reperfusion, and/or applying a different or more complicated combination of medications to the subject, leads to better patient outcomes. Based on this existing research, being able to estimate the approximate time of the onset of ventricular fibrillation can improve patient outcomes and help a clinician select a preferred treatment protocol based on the down time.

Figure 10:
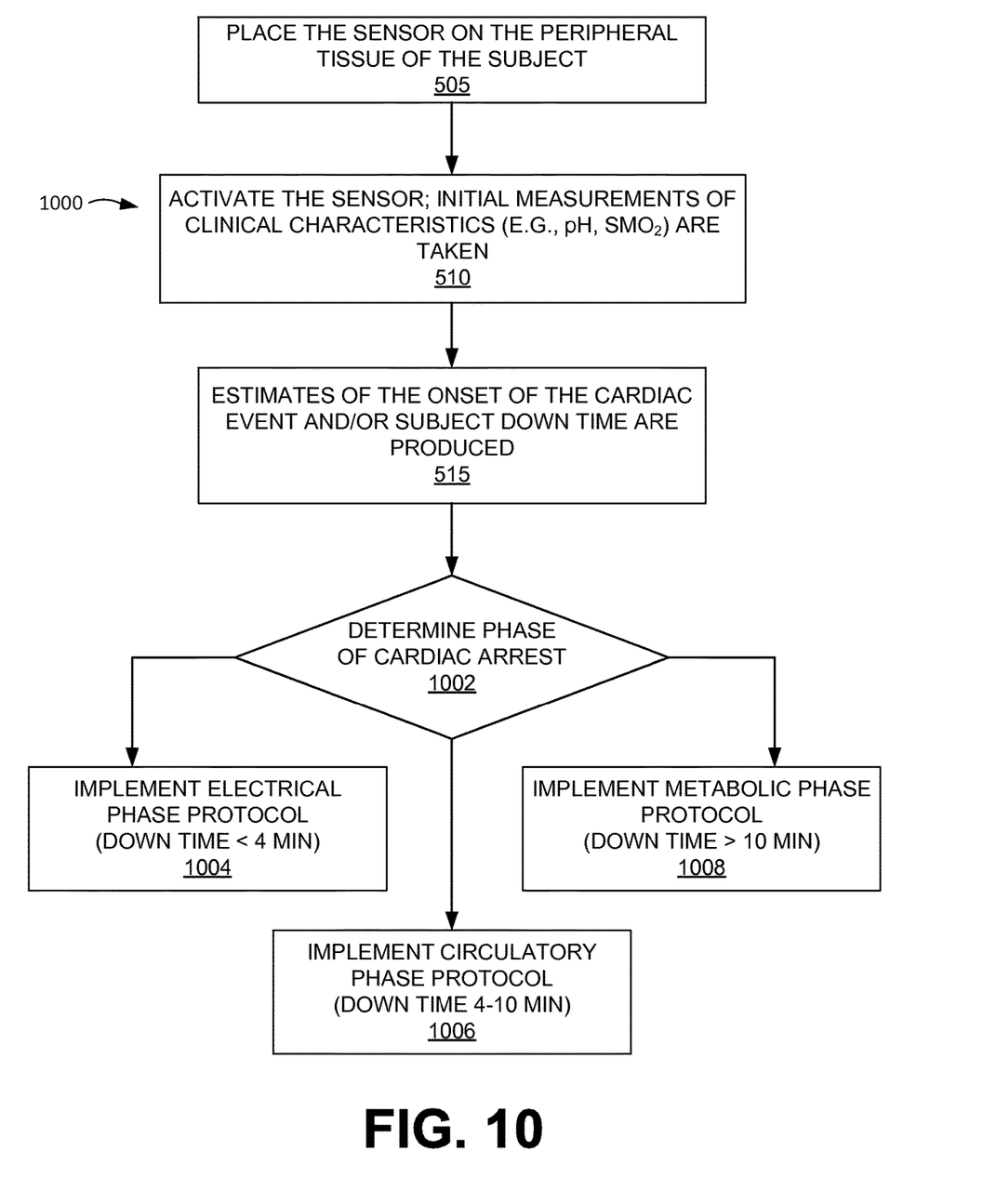
FIG. 10 is a flow chart representing a method of administering emergency treatment to a subject experiencing a cardiac event, according to one embodiment of the present disclosure.

FIG. 10 illustrates a method that estimates subject down time to determine which of the three phases of cardiac arrest a subject is in and to select a treatment protocol accordingly. All or parts of this method may be implemented by processor 116 of FIG. 3, including receiving sensor measurements from sensor assembly 102 and/or displaying information/data or implementing treatment protocols on other devices (e.g. devices 114, 118, 120, 124, 126, 128, and/or 130). Blocks 505, 510, and 515 are similar to as described above with respect to FIG. 5. However, FIG. 5 describes a "two phase" approach, while FIG. 10 describes a three-phase approach. At block 1002, a determination is made as to which of three phases the subject is in, based on the subject's estimated down time. This may be done using observations or measurements of the subject's pH, $SmO_2$, or a combination of pH and $SmO_2$, for example using Equations 1 and/or 2 described above, which would give possible cutoff values for pH of 7.22 and SmO2 values of 25.5% to indicate a cutoff for the end of the electrical phase. If the subject's down time is approximately less than four minutes, an electrical phase treatment protocol may be implemented (block 1004), for example by immediately commencing defibrillation on the subject. If the subject's down time is approximately four minutes to ten minutes, a circulatory phase treatment protocol may be implemented (block 1006), for example by conducting cardiopulmonary resuscitation (for example using CPR device 130 of FIG. 3) or cardiopulmonary resuscitation along with epinephrine administration prior to defibrillation. Using, for example, Equations 1 and/or 2 described above would give possible cutoff values for pH of 7.15 and $SmO_2$ values of 18% to indicate a cutoff for the end of the circulatory phase or start of a metabolic phase. If the subject's down time is approximately greater than ten minutes, a metabolic phase treatment protocol may be implemented (block 1008), for example by applying cooling therapy to the subject prior to reperfusion therapy. For example, if the subject's pH were less than about 7.15, and/or the subject's $SmO_2$ were less than about 18%, the subject's down time would be expected to be greater than 10 minutes (or 600 seconds), as illustrated by the graphical representations of FIGS. 8 and 9. As one non-limiting example, if a subject who is known to have experienced a ventricular fibrillation event has a pH of less than about 7.15 and/or an $SmO_2$ of less than about 18%, a medical device could alert the user that thermal or temperature management therapy (for example using temperature management device 128 of FIG. 3) should be immediately commenced, and/or a special metabolic drug cocktail delivered to the subject, rather than immediately shocking the subject or performing CPR.

According to some embodiments, the subject down time may be estimated based on both pH measurements and $SmO_2$ measurements. Such subject down time estimations may be compared, for example to validate the data by determining whether the down time calculation made with pH is within a predetermined threshold or threshold percentage of the down time calculation made with $SmO_2$, according to some embodiments. According to some embodiments, the down time calculated with the pH may be averaged with the down time calculated with the $SmO_2$, and the averaged down time may be used to determine the cardiac arrest phase and/or determine whether to administer CPR and/or defibrillation. Such averaging may be done after the validation comparison, for example.

Additionally, one of ordinary skill in the art would appreciate that the phases mentioned above are based on physiological models. One skilled in the art would recognize that cut off values for pH and oxygenation levels may vary across animal populations, for example, younger and healthier subjects might have better oxygen reserves and therefore may stay in the electrical phase longer than an older subject with other co-morbidities and disease. Thus, one skilled in the art would recognize that the above hypothesized time ranges for each respective phase of cardiac arrest within a given individual subject will vary, for example, such time ranges may vary by as high as twenty percent from those described above. Additionally, one skilled in the art would recognize that additional information could be used to determine the phase of cardiac arrest. For example, such additional information could include invasive measurements of oxygen consumption in the heart muscle, non-invasive measurements of heart oxygenation via NIRS sensors on the chest and/or in the esophagus, skin color of a subject, and/or examining the electrocardiogram to determine if the ventricular fibrillation (VF) waveform has high amplitude and frequency (suggestive of a shorter downtime or shorter duration of VF) or low amplitude and frequency (suggestive of longer downtime or longer duration of VF that might be transitioning to asystole), etc.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. An external system for deriving an indication of subject down time for a patient having experienced a cardiac arrest event, the system comprising:
    a spectral sensor, wherein the spectral sensor is configured for external placement on skin of a subject above muscle tissue of the subject;
    a memory; and
    a processor communicably coupled to the spectral sensor and the memory, the memory including instructions that, when executed by the processor, cause the processor to:
        determine at least one of muscle oxygen saturation of the muscle tissue with the spectral sensor and pH of the muscle tissue with the spectral sensor,
        estimate a duration of the subject down time since an onset of the cardiac arrest event, the duration of the subject down time determined based on at least one of the muscle oxygen saturation and the pH of the muscle tissue,
        determine a phase of cardiac arrest based on the estimated duration of the subject down time, and
        provide guidance for implementation of a treatment protocol based on the determined phase of cardiac arrest.

2. The system of claim 1, wherein the phase is a circulatory phase.

3. The system of claim 2, further comprising a defibrillator wherein the memory further includes instructions that, when executed by the processor, cause the processor to provide guidance for implementing a treatment protocol by instructing a user to activate the defibrillator.

4. The system of claim 3, further comprising a CPR device, wherein the memory further includes instructions that, when executed by the processor, cause the processor to provide guidance for implementing the treatment protocol by instructing the user to activate the CPR device.

5. The system of claim 4, further comprising a display device, wherein the memory further includes instructions that, when executed by the processor, cause the processor to display on the display device an indication of the phase and an instruction to conduct CPR prior to defibrillation.

6. The system of claim 4, wherein the determined subject down time is approximately four to ten minutes.

7. The system of claim 1, wherein the phase is an electric phase.

8. The system of claim 7, further comprising a defibrillator, wherein the memory further includes instructions that, when executed by the processor, cause the processor to provide guidance for implementing a treatment protocol by instructing a user to activate the defibrillator.

9. The system of claim 8, wherein the determined subject down time is less than four minutes.

10. The system of claim 1, wherein the phase is a metabolic phase.

11. The system of claim 10, further comprising a temperature management device, wherein the memory further includes instructions that, when executed by the processor, cause the processor to provide guidance for implementing the treatment protocol by instructing a user to activate the temperature management device.

12. The system of claim 11, wherein the determined subject down time is greater than ten minutes.

13. The system of claim 1, wherein the spectral sensor comprises two or more long-distance radiation sources, one or more short-distance radiation sources, and a spectral detector.

14. The system of claim 13, wherein at least two of the two or more long-distance radiation sources and at least one of the one or more short-distance radiation sources are located on the spectral sensor at different distances from the spectral detector.

15. The system of claim 1, wherein the memory further includes instructions that, when executed by the processor, cause the processor to estimate the duration of the subject down time based on a predetermined quantitative correlation between at least one of:
    subject down time and muscle oxygen saturation; and
    subject down time and muscle tissue pH.

16. The system of claim 1, further comprising a display device, the memory further includes instructions that, when executed by the processor, cause the processor to visually indicate the estimated duration of the subject down time.

17. The system of claim 1, wherein the spectral sensor comprises one or more long distance radiation sources and one or more short-distance radiation sources, and a spectral detector.

* * * * *